United States Patent [19]

Thiel

[11] Patent Number: 5,129,952
[45] Date of Patent: Jul. 14, 1992

[54] DISPERSED CERAMIC COMPOSITION AND PROCESS FOR PREPARING IT

[75] Inventor: Norbert Thiel, Bad Sackingen, Fed. Rep. of Germany

[73] Assignee: Vita Zahnfabrik H. Rauter GmbH & Co., Bad Sackingen, Fed. Rep. of Germany

[21] Appl. No.: 645,181

[22] Filed: Dec. 20, 1990

Related U.S. Application Data

[63] Continuation-in-part of Ser. No. 000,677, Jun. 16, 1989.

[30] Foreign Application Priority Data

Jun. 21, 1988 [DE] Fed. Rep. of Germany ....... 3820839

[51] Int. Cl.$^5$ .................... C04B 35/00; A61K 6/00
[52] U.S. Cl. ........................................ 106/35; 501/1; 433/223
[58] Field of Search ............... 501/1; 106/35; 433/223

[56] References Cited

U.S. PATENT DOCUMENTS

| | | | |
|---|---|---|---|
| 4,097,935 | 7/1978 | Jarcho | 501/1 |
| 4,626,392 | 12/1986 | Kondo et al. | 501/1 |
| 4,629,464 | 12/1986 | Takata et al. | 501/1 |

FOREIGN PATENT DOCUMENTS

| | | |
|---|---|---|
| 0185597 | 6/1986 | European Pat. Off. . |
| 292406 | 6/1916 | Fed. Rep. of Germany . |
| 1296301 | 5/1969 | Fed. Rep. of Germany . |
| 2534504 | 2/1976 | Fed. Rep. of Germany . |
| 2620694 | 11/1976 | Fed. Rep. of Germany . |
| 3638065 | 5/1987 | Fed. Rep. of Germany . |
| 263406 | 1/1989 | Fed. Rep. of Germany . |

OTHER PUBLICATIONS

Phillips, *Skinners Science of Dental Materials*, Chapter 31 pp. 526–530.
Schwickerath, "Werkstofk in Der Zahnheilkunder" p. 118 Quintessenz (1977).
Eichner, "Metallkeramik in der Zahnarztlichen Prothetik", p. 29 (1979).

*Primary Examiner*—William R. Dixon, Jr.
*Assistant Examiner*—Anthony J. Green
*Attorney, Agent, or Firm*—Wegner, Cantor, Mueller and Player

[57] ABSTRACT

The dispersed ceramic composition for the manufacture of ceramic teeth, bridges and crowns in a dental technician's laboratory consists of a sinterable ceramic powder and a dispersing liquid and comprises a liquid consisting of a solution of from 0.05 to 5% by weight of one or more thickening agents from the group of cellulose, cellulose derivatives, tragacanth, xanthan gum and alginates in water, lower alcohols and/or other readily volatile organic solvents, while modifying additives may have optionally been added to said dispersed ceramic composition and the content of liquid is from 10 to 50% by weight of the ceramic composition.

7 Claims, No Drawings

DISPERSED CERAMIC COMPOSITION AND PROCESS FOR PREPARING IT

This application is a continuation-in-part under 35 USC §120 and §365 of U.S. application Ser. No. 89/00677, filed Jun. 16, 1989 pending.

The present invention relates to a dispersed ceramic composition for the manufacture of ceramic teeth, bridges and crowns in a dental technical laboratory, consisting of a sinterable ceramic powder and a dispersing liquid.

Such ceramic compositions so far have been produced in the dental laboratory from the commercially available sinterable ceramic powders and distilled water or modelling liquids offered in combination with the ceramic powders. From the German Laid Open Patent Application (DE-OS) 36 38 065 and the U.S. Pat. No. 4,645,454 it is already been known to employ organic solvents having a relatively high boiling point as the dispersing liquid, the index of refraction of which is in the proximity of the index of refraction of the ceramic powder. This already allows a judgment during the manufacture of how the unfired ceramic composition will appear once it will have been fired. Some of the organic solvents proposed are already so viscous that the ceramic paste becomes too thick. Thus, if need be, a mixture of solvents will have to be used in order to keep the viscosity coefficient below 20 mPa s. In the U.S. Pat. No. 4,645,454 it has further been mentioned that it is basically possible to mix the organic solvent and the ceramic powder in advance and to market the pre-fabricated mix in a packaged form. However, such mixtures so far have not yet been marketed. A substantial drawback of the organic solvents so far proposed is the strong odor problem during work, the relatively high toxicity, especially since dental technicians tend to take their brushes into their mouths, and the strong odor nuisance in the laboratory in the course of the subsequent step of finally firing the compositions in a sintering furnace, which could not be used without a fume hood in the dental laboratory.

From DE-OS 25 34 504 there is known a ceramic material which is suitable for the preparation of a polycrystalline sintered ceramic material or sintered ceramics, in the preparation of which calcium ions are precipitated with phosphate ions in an aqueous medium at a pH of from 10 to 12 and the resulting precipitates are sintered at a temperature of at least 1000° C. In order to increase the porosity, an organic binder such as cellulose or collagen is admixed to the precipitate which completely volatilizes upon firing. These materials are unsuitable for the manufacture of ceramic teeth, bridges and crowns in the dental laboratory, since generally only temperatures of between 930° C. and 960° C. are employed. The same applies to the powder composition for the manufacture of commercially available false teeth, which also are fired in general at about 1200° C. for about 15 to 20 minutes. Thus, if organic dyes or organic binders such as starch or oil are admixed to such powder compositions, they can be burned considerably more readily at the temperatures employed.

The same is true for porous ceramic or metal coatings and products of DE-OS 26 20 694, wherein even temperatures of 1600° C. are employed. However, in the dental technical laboratory, mostly temperatures of only 930° C. to 960° C. are employed for 2 minutes, so that it will have to be taken into account that high polymer substances will undergo only incomplete combustion or no combustion at all.

It is the object of the present invention to develop prefabricated dispersed ceramic compositions for the manufacture of ceramic teeth, bridges and crowns in a dental technical laboratory, which compositions consist of a sinterable ceramic powder and a dispersing liquid, which do not exhibit the above-mentioned drawbacks. Prefabricated dispersed ceramic compositions have the advantage over the currently conventional sinterable ceramic powders, which always have to be first dispersed by hand with distilled water or with the above-mentioned organic solvents, in that no mistakes caused by inappropriate mixing ratios will occur and that the time required for dispersing will be saved. It was now found that this object can be attained in a surprisingly easy way by a liquid consisting of a solution of from 0.05 to 5% by weight of one or more thickening agents selected from the group of cellulose, cellulose derivatives, tragacanth, xanthan gum and alginates in water, lower alcohols and/or other relatively volatile organic solvents; modifying additives may be optionally added to these dispersed ceramic composition and the liquid content is from 10 to 50% by weight of the ceramic composition.

It was surprising that these thickening agents usable according to the invention can be removed rapidly and without leaving adverse residues already upon firing at from 930° C. to 960° C. within 2 minutes without any deterioration of the mechanical or optical properties of the fired material. Although the thickening agents used in the invention are known to be of relatively high molecular weight and during combustion to tend to first carbonize and form carbon black thereby, it was now found that on use as an additive to the dispersed ceramic composition for the dental technical laboratory they can be removed in the subsequent firing operation virtually without leaving any residue. It is another advantage that in the course of the firing they burn virtually odor-free so that it is still possible in the dental laboratory to employ firing furnaces without a fume hood. The thickening agents used according to the invention, on the other hand, are capable of being employed individually or in the form of mixtures and thereupon to bind the solvent employed and to control the viscosity in such a manner that dispersed ceramic compositions are formed which - even if exposed to the air for an extended period of time - are well processable. It is only in the course of the subsequent drying and firing operations at elevated temperatures that the solvent and the thickening agent are removed and/or burned. It is another advantage of the thickening agents of the invention that, if so desired, they may be admixed with somewhat more solvent by the dental technician who, thus, is enabled to individually adjust the optimal viscosity and processability of the material for himself.

The dispersing liquid for the ceramic composition contains from 0.05 to 5% of the thickening agent. The ceramic compositions preferably contain from 0.2 to 3% by weight of binder. The optimal amount also is determined, i.a., by how much of the dispersing liquid, relative to the amount of sinterable ceramic, is to be employed. The content of dispersing liquid in the final ceramic compositions is from 10 to 50% by weight. Preferably the amount of liquid is from 15 to 30% by weight, since such composition are particularly well processable with a spatula or brush.

Modifying additives such as plasticizers and surfactants may optionally be admixed to the dispersed ceramic compositions according to the invention. Further additives within this meaning, for example, are stabilizers which inhibit growth of bacteria and fungi. Further additives include glycols, by means of which it is possible to vary the consistency, shapability, firmness, moisture loss and stability within wide limits.

The new dispersed ceramic compositions may be handled with a spatula or brush in the same manner as the plastic composition also conventionally used today. Thus, it is also possible to have the work carried out by staff familiar with processing plastic compositions. This offers further savings in time and costs. It is further possible to prepare the ceramic compositions of the invention in the dental laboratory from prefabricated dry mixtures consisting of the ceramic powder and the appropriate thickening agent by adding the appropriate mixing liquid, if these mixtures have been obtained by allowing a dispersion of the invention comprising ceramic powder and a solution of the thickening agent to dry. If, however, the dry ceramic powder and the dry thickening agents are only mixed with each other in the dry state and the resulting mixtures are stirred in the solvent, then dispersed ceramic compositions are obtained which in general are only very poorly workable.

These dried mixtures, comprising ceramic composition and thickening agents obtained by allowing the dispersion to dry, are suitable of being quickly, readily and reliably mixed with water, lower alcohols and/or other volatile organic solvents and, thus, of being reconverted into the dispersed ceramic composition. It has been shown that the dispersed ceramic compositions thus obtained again conform to the original dispersed ceramic compositions. They are mixed considerably easier, simpler and more reliably by a dental technician than are pure ceramic compositions with a solvent without the thickening agents used according to the invention.

A technically important advantage of these dried compositions comprising thickening agents is that they are easier to dispense and package, to store and to transport than ready-to-use dispersed ceramic compositions. It is true, these dried-up ceramic compositions comprising thickening agents will have to be mixed with the solvent as was the case previously with the pure ceramic compositions; however, now this is much more easily feasible due to the addition of the thickening agents, since the amount of solvent used is less critical than with pure ceramic powders and the respective modelling liquids. Another essential advantage consists in the improved plastic properties of these compositions and, hence, the possibility of using the so-called spatula technique which otherwise is employed in the field of dental plastics.

Some embodiments of the dispersed ceramic compositions are illustrated in the following Examples.

EXAMPLE 1

12 g of a commercially available sinterable ceramic powder of Vita Zahnfabrik H. Rauter GmbH & Co., (VMK 68-Dentin 552) were stirred with 3 g of an aqueous solution to form a pasty mass, said solution consisting of a 1.5% aqueous solution of a xanthan gum derivative (Rhodegel 23/Rhone-Poulenc) which had been mixed with 5% of 1,3-butanediol. A well processable ceramic composition was obtained which could be dried and fired in the conventional manner (2 minutes at 930° C. to 960° C.) and corresponded with respect to the mechanical and optical properties completely to those products prepared with only distilled water as the dispersing liquid. Also an addition of 1% of stabilizing agents such as Rokonsal KS, Euxyl K 400, Acticid SPX or formaldehyde did not change the processing properties, but resulted in that the pre-fabricated dispersed ceramic composition did not permit any growth of bacteria or fungi even over an extended period of time. Thus, the resulting mixture, when stored under air-tight and cool conditions, is storable for a long time but nevertheless directly usable at any time.

EXAMPLE 2

30 g of a commercially available sinterable ceramic powder of Vita Zahnfabrik H. Rauter GmbH & Co., (VMK 68-Schmelz 55g) were stirred with 7 g of a 1.2% nitrocellulose solution (E 1440, Wolff, Walsrode) in isoamyl acetate to form a paste. This material also was readily processable and provided unobjectionable products, if it was pre-dried for some time before firing. The shrinkage was only 13.2%, whereas it is about 18% with the compositions according to the U.S. Pat. No. 4,645,454.

EXAMPLE 3

720 g of a commercially available sinterable ceramic powder of Vita Zahnfabrik H. Rauter GmbH & Co., (VMK 68-Dentin 546) were mixed with 220 g of a 2% aqueous solution of hydroxypropylmethylcellulose (Methocel F4M/Dow Chemical) and 20 g of 1,5-pentadiol to form a readily spreadable paste. This paste was readily processable and after drying and firing gave unobjectionable products which absolutely corresponded to those prepared only with distilled water.

EXAMPLE 4

12 g of a commercially available sinterable ceramic powder of Vita Zahnfabrik H. Rauter GmbH & Co., (VMK 68-Schmelz 559) were stirred with 3 g of a 1.5% aqueous solution of hydroxybutylcellulose (Methocel HB/Dow Chemical) and 1 g of distilled water to form a paste. This paste was well processable and after drying and firing provided excellent products.

EXAMPLE 5

24 g of a commercially available sinterable ceramic powder of Vita Zahnfabrik H. Rauter GmbH & Co., (VMK-Dentin 554) were stirred with 3 g of a 1.5% aqueous solution of a xanthan gum derivative (Rhodegel 23/Rhone-Poulenc) as well as with 3 g of a 2 % solution of hydroxypropylmethyl-cellulose (Methocel F4M/Dow Chemical) and 2 g of distilled water to form a paste. This paste was excellently processable and after drying and firing provided good results.

EXAMPLE 6

16 g of a commercially available sinterable ceramic powder of Vita Zahnfabrik H. Rauter GmbH & Co., (VMK-Dentin 552) were stirred with 5 g of a 4% aqueous-alcoholic suspension of tragacanth (water:alcohol=1:1) and 2.5 g of water to form a spreadable paste. The consistency of the resulting mass was improved by 24 hours of storage. Also from this mass good products could be formed which absolutely conformed to the products prepared only with distilled water.

The mixtures of the Examples 2 through 6 could also be preserved by the addition of common stabilizers and could be optimized with respect to the processability by the addition of glycols.

EXAMPLE 7

96 g of a commercially available sinterable ceramic powder of Vita Zahnfabrik H. Rauter GmbH & Co., (VMK 68 N - Dentin 252) were worked up with a kneader into a spreadable paste with 12 g of a 1.5% aqueous solution of a xanthan gum derivative (Rhodegel 23/Co. Rhone-Poulenc) and 12 g of a 2 % aqueous solution of hydroxypropylmethylcellulose (Methocel F4M/Dow Chemical) and 8 g of distilled water. The resulting mass was spread over a large surface area and dried at room temperature for 48 hours. Then the mass was stirred in a mortar to form a powder. This powder was capable of being mixed with distilled water to give a paste of the initial consistency within a short time.

For comparison, 96 g of the same ceramic powder was mixed in the dry state with 0.1 g of xanthan gum derivative and 0.24 g of hydroxypropylmethylcellulose. In an attempt to mix and stir the resulting product with the appropriate amount of distilled water, unusable products were obtained. Also grinding the cellulose, followed by sifting and dry admixing the obtained finer grains, did not lead to a success.

EXAMPLE 8

12 g of a commercially available sinterable ceramic powder of Vita Zahnfabrik H. Rauter GmbH & Co., (VMK 68 N - Dentin 552) were stirred with 3 g of a 1.5% aqueous solution of hydroxybutylcellulose (Methocel HB/Co. Dow Chemical) and 1 g of distilled water with an agate or glass spatula on a glass plate to form a paste. The resulting composition was dried at 80° C. in a drying oven with air circulation for 4 hours. Then the mass was ground in a mortar to give a powder. This powder was capable of being mixed with distilled water to give an easily processable paste.

For comparison, the same amount of ceramic powder was thoroughly mixed in the dry state with 0.045 g of hydroxybutylcellulose. In the attempt of mixing and stirring the resulting mixture with water, unusable products were obtained.

EXAMPLE 9

The dried powders obtained according to the Examples 7 and 8 were stirred and mixed using a mixture of 95% of distilled water and 5% of butanediol in the place of distilled water. Well processable pastes were thus also obtained within a short time, which pastes provided unobjectionable products after drying and firing.

I claim:

1. A dispersed ceramic composition for the manufacture of ceramic teeth, bridges and crowns comprising a sinterable ceramic powder and a dispersing liquid, wherein the dispersing liquid comprises a solution of 0.05 to 5% by weight of one or more thickening agents selected from the group of cellulose, cellulose derivatives, tragacanth, xanthan gum and alginates in water, a readily volatile organic solvent, or a combination of water and a readily volatile organic solvent, wherein said composition is sinterable at temperatures below 960° C. for not more than about 2 minutes.

2. Ceramic composition according to claim 1, wherein the content of liquid is 10–50% by weight of the ceramic composition.

3. A ceramic composition according to claim 1, wherein the readily volatile organic solvent is a lower alcohol.

4. Ceramic composition according to claim 1, wherein the viscosity of the ceramic composition is adjustable by the addition of said solvent.

5. The dispersed ceramic composition of claim 1 which is useful for the manufacture of ceramic teeth, bridges or crowns in a dental technician's laboratory, wherein the dispersing liquid is completely removed when said composition is fired at temperatures of about 930° C. to 960° C.

6. A dry ceramic composition for the manufacture of ceramic teeth, bridges and crowns comprising a sinterable ceramic powder and one or more thickening agents, wherein said dry ceramic composition is formed by allowing a dispersed ceramic composition to dry up, wherein said dispersed ceramic composition comprises a sinterable ceramic powder and a dispersing liquid, wherein the dispersing liquid comprises a solution of 0.05 to 5% by weight of one or more thickening agents selected from the group consisting of cellulose, cellulose derivatives, tragacanth, xanthan gum and alginates in water, a readily volatile organic solvent, or a combination of water and a readily volatile organic solvent, wherein said dispersed ceramic composition is sinterable at temperatures below 960° C. for not more than about 2 minutes.

7. A method of preparing ceramic teeth, bridges or crowns comprising molding a dispersed ceramic composition according to claim 1 in the shape of ceramic teeth, bridges or crowns, and sintering the molded composition at temperatures below 960° C. for not more than about 2 minutes.

* * * * *